United States Patent [19]

Harwood et al.

[11] 4,439,194
[45] Mar. 27, 1984

[54] WATER AND DRUG DELIVERY SYSTEM FOR SUPPOSITORY USE

[75] Inventors: Richard J. Harwood, Bensalem; Joseph V. Bondi, Collegeville, both of Pa.

[73] Assignee: Merck & Co., Inc., Rahway, N.J.

[21] Appl. No.: 300,370

[22] Filed: Sep. 8, 1981

[51] Int. Cl.$^3$ ............................................. A61L 15/06
[52] U.S. Cl. ..................................................... 604/890
[58] Field of Search ............... 128/260; 604/890, 891, 604/892–896, 56, 285–288, 364, 904; 424/19–22, 24–26

[56] References Cited

U.S. PATENT DOCUMENTS

| | | | |
|---|---|---|---|
| 1,573,976 | 12/1896 | Hinchman | 604/287 |
| 1,812,769 | 2/1906 | Pond | 604/287 |
| 2,110,962 | 3/1938 | Munro | 604/890 |
| 3,490,454 | 1/1970 | Goldfarb et al. | 604/359 |
| 3,521,637 | 7/1970 | Waterbury | 604/286 |
| 3,845,770 | 11/1974 | Theeuwes et al. | 128/260 |
| 3,967,618 | 7/1976 | Zaffaroni | 128/260 |
| 3,977,404 | 8/1976 | Theeuwes | 128/260 |
| 4,160,452 | 7/1979 | Theeuwes | 128/260 |

OTHER PUBLICATIONS

Australian Journal of Experimental Biology, vol. 33, pp. 415–420 (1955), "A Continuous Long-Term Injector".

Primary Examiner—C. Fred Rosenbaum
Assistant Examiner—T. J. Wallen
Attorney, Agent, or Firm—Rudolph J. Anderson, Jr.; Mario A. Monaco; Michael C. Sudol, Jr.

[57] ABSTRACT

A drug delivery system designed to deliver water and drug to the site of administration is composed of a core of an aqueous solubulizing system in a wax housing, which melts at body temperature, surrounded by a matrix of drug and water-dispersible excipients. The entire unit may also be coated with a semi-permeable membrane to modulate drug release.

5 Claims, 3 Drawing Figures

WATER AND DRUG DELIVERY SYSTEM FOR SUPPOSITORY USE

BACKGROUND OF THE INVENTION

This invention is concerned with a drug delivery system primarily intended for, but not limited to, use in an environment which is normally low in available body fluid volume such as the rectal or vaginal cavity. The novel design is particularly suitable for its intended use inasmuch as the water necessary for dissolution of the active ingredients is provided as an integral part of the novel drug delivery system.

Drug delivery systems carrying their own water are known in the art and one such device is disclosed in *Austral. J. Exp. Biol.*, 33, 415 to 420, (1955). This device consists of three compartments confined in a specifically constructed housing and a clamp to hold a semi-permeable membrane. The driving force of the device depends on the continual presence of a solution of an osmotically effective red dye solute that exhibits an osmotic pressure gradient against water. The red dye is contained in a partially collapsed rubber compartment and it is separated from a second compartment containing water by a semi-permeable membrane. The partially collapsed bag is housed in a glass ampoule, along with a product compartment defined by the space between the bag and one end of the glass ampoule. The distant end of the ampoule defines a water compartment. The ampoule also is provided with a drug release nipple, and in operation when the product compartment is charged with a solution of a product, water in the water compartment moves through the semi-permeable membrane into the dye solution increasing its volume in the compartment causing it to expand against the rubber providing the mechanical force necessary to eject the product solution through the nipple. It is immediately evident that this device has certain adverse features that tend to diminish its practical use. For example, the device is difficult to construct into compartments that are essentially free of leaks and because of the fabrication demands of a movable material that necessitates a rigid outer housing. Another inherent disadvantage which prevented its wide acceptance by the medical community is the requirement that the drug be in solution. Such solutions tend to be released from the device by simple leaching; they do not permit high concentrations of the product to be embodied within the device; they often promote chemical deterioration of the active drug; and they do not permit the use of insoluble or poorly soluble drugs.

It is an object of this invention to provide a drug delivery system comprising a core of aqueous solubulizing system in a wax housing which melts at body temperature surrounded by a matrix of drug and water dispersible excipients which may also be coated with a semi-permeable membrane to modulate release of drug solution.

It is a further object of this invention to provide such a system primarily for use in an environment low in body fluid volume such as the rectal cavity.

It is also an object of this invention to provide a novel drug delivery system that is simple and easy to construct, that carries its own water, and in which the drug is in solution only after administration of the device.

DETAILED DESCRIPTION OF THE DRAWINGS

The drawings are examples of devices of the invention and portions thereof and are not to be construed as limiting.

DETAILED DESCRIPTION OF THE INVENTION

Figure 1:
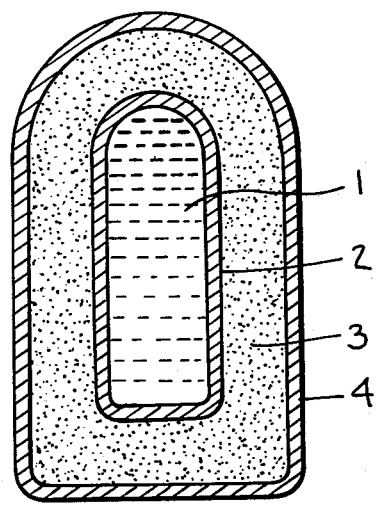
FIG. 1 represents a complete device of the invention in cross-section, showing the aqueous core 1, surrounded by the wax housing, 2, which melts at body temperature, which in turn is surrounded by a matrix of drug and water-dispersible excipients, 3, which in turn is optionally surrounded by a coating, 4.

The novel drug delivery system of this invention comprises a core of water in a wax housing which melts at body temperature surrounded by a matrix of drug, water soluble or dispersible excipients and optionally, osmotic-active agents, which in turn is optionally surrounded by a coating which optionally can be semi-permeable.

The water of the aqueous core can be neat, an aqueous buffer, or other aqueous solubulizing system or it can be in the form of an aqueous cross-linked polymeric gelatinous pellet. The volume of available water can vary widely depending on the solubility and amount of drug to be delivered and on the site of delivery, but usually is between about 0.1 ml and 3 ml.

The waxy housing of the aqueous core is composed of a water-insoluble, low melting (35°–37° C.) material selected from theobroma oil, SUPPOCIRE A ® (an eutectic mixture of mono-, di-, and triglycerides supplied by A. & S. Corporation, Verona, N.J., U.S.A.), WECOBEE R ® (higher melting fractions of coconut oil and palm kernel oil, supplied by Drew Chemical Corp., Boonton, N.J., U.S.A.) and WITEPSOL S55 ® (Triglyceride of saturated vegetable fatty acids with monoglycerides, supplied by Riches-Nelson Inc., New York, N.Y., U.S.A.).

The matrix surrounding the aqueous core has an outer shape and dimensions of conventional rectal or vaginal suppositories and comprises a mixture of one or more drugs and pharmaceutically acceptable water soluble and/or dispersible ingredients.

Any of the drugs used to treat the body can be incorporated as the drug of the delivery device of this invention. "Drug" is used herein in its broadest sense as including any composition or substances that will produce a pharmacologic response.

Suitable drugs for use in therapy with the device of the invention include without limitation:

1. Protein drugs such as insulin;
2. Desensitizing agents such as ragweed pollen antigens, hay fever pollen antigens, dust antigen and milk antigen;
3. Vaccines such as smallpox, yellow fever, distemper, hog cholera, fowl pox, antivenom, scarlet fever, dyptheria toxoid, tetanus toxoid, pigeon pox, whooping cough, influenzae, rabies, mumps, measles, poliomyelitis, Newcastle disease, etc.;

4. Antiinfectives, such as antibiotics, including penicillin, tetracycline, chlortetracycline bacitracin, nystatin, streptomycin, neomycin, polymyxin, gramicidin, oxytetracycline, chloramphenicol, and erythromycin; sulfonamides, including sulfacetamide, sulfamethizole, sulfamethazine, sulfadiazine, sulfamerazine, and sulfisoxazole, cefoxiton; anti-virals including idoxuridine; and other anti-infectives including nitrofurazone and sodium propionate;

5. Antiallergenics such as antazoline, methapyrilene, chlorpheniramine, pyrilamine and prophenpyridamine;

6. Steroidal anti-inflammatory agents such as hydrocortisone, cortisone, hydrocortisone acetate, dexamethasone, dexamethasone 21-phosphate, fluocinolone, triamcinolone, medrysone, prednisolone, prednisolone 21-phosphate, and prednisolone acetate;

7. Decongestants such as phenylephrine, naphazoline, and tetrahydrazoline;

8. Miotics such as pilocarpine, eserine salicylate, carbachol, diisopropyl fluorophosphate, phospholine iodide, and demecarium bromide;

9. Anticholinergics such as atropine sulfate, cyclopentolate, homatropine, scopolamine, tropicamide, eucatropine, and hydroxyamphetamine;

10. Sympathomimetics such as epinephrine;

11. Sedatives and Hypnotics such as pentabarbital sodium, phenobarbital, secobarbital sodium, codeine, ($\alpha$-bromoisovaleryl)urea, carbromal;

12. Psychic Energizers such as 3-(2-aminopropyl)indole acetate, 3-(2-aminobutyl)indole acetate and amitriptyline;

13. Tranquilizers such as reserpine, chlorpromazine, thiopropazate and perphenazine;

14. Androgenic steroids such as methyltestosterone and fluorymesterone;

15. Estrogens such as estrone, 17 $\beta$-estradiol, ethinyl estradiol, and diethyl stilbesterol;

16. Progestational agents such as progesterone, megestrol, melengestrol, chlormadinone, ethisterone, norethynodrel, 19-nor-progesterone, norethindrone, medroxyprogesterone and 17 $\beta$-hydroxy-progesterone;

17. Humoral agents such as the prostaglandins, for example $PGE_1$, $PGE_2$ and $PGF_2$;

18. Antipyretics analgesics such as aspirin, sodium salicylate, salicylamide, and diflunisal;

19. Antispasmodics such as atropine, methantheline, papaverine, and methscopolamine bromide;

20. Antimalarials such as the 4-aminoquinolines, 8-aminoquinolines, chloroquine, and pyrimethamine;

21. Antihistamines such as diphenhydramine, dimenhydrinate, tripelennamine, perphenazine, and chlorophenazine;

22. Cardioactive agents such as dibenzhydroflumethiazide, flumethiazide, hydrochlorothiazide, chlorothiazide, and aminotrate;

23. Non steroidal anti-inflammatory agents such as indomethacin, and sulindac;

24. Antiparkinsonian agents such as L-dopa;

25. Antihypertensive agents such as methyldopa;

26. $\beta$-Adrenergic blocking agents such as propanolol and timolol;

27. Nutritional agents such as vitamins, essential amino acids and essential fats.

Other drugs having the same or different physiological activity as those recited above can be employed in drug-delivery devices within the scope of the present invention.

Drugs can be in various forms, such as uncharged molecules, components of molecular complexes, or nonirritating, pharmacologically, pharmaceutically acceptable salts such as hydrochloride, hydrobromide, sulfate, phosphate, nitrate, borate, acetate, maleate, tartrate, salicylate, etc. For acidic drugs, salts of metals, amines, or organic cations (e.g., quaternary ammonium) can be employed. Furthermore, simple derivatives of the drugs (such as ethers, esters, amides, etc.) which have desirable retention and release characteristics but which are easily hydrolyzed by body pH, enzymes, etc., can be employed.

The amount of drug incorporated in the drug-delivery device varies widely depending on the particular drug, the desired therapeutic effect, and the time span for which it takes the film barrier and matrix material to erode or dissolve. Since a variety of devices in a variety of sizes and shapes are intended to provide complete dosage regimens for therapy for a variety of maladies, there is no critical upper limit on the amount of drug incorporated in the device. The lower limit too will depend on the activity of the drug and the time span of its release from the device. Thus it is not practical to define a range for the therapeutically effective amount of drug to be released by the device.

The pharmaceutically acceptable water-soluble and/or dispersible ingredients of the matrix serves to give the suppository shape and rigidity and to preserve the integrity of the device prior to use. These materials include such as polyethylene glycol, gelatin, starch, lactose, cellulosic derivatives, or the like, materials well known in the pharmaceutical industry.

In addition to the drug and water-dispersible agent, the matrix may also contain an absorption promoter or adjuvant such as salicylic acid or derivatives, benzalkonium chloride, sodium glycocholate or the like. If sustained, prolonged or pulsed release characteristics are desired the matrix may also include osmotic active agents such as sodium chloride, mannitol, sucrose or other agent selected from those described in U.S. Pat. No. 3,977,404. In this case the device is coated with a semi-permeable film such as cellulose acetate, polyvinyl acetate or ethylenevinyl acetate commonly used in the osmotic delivery systems.

Preparation of the novel drug delivery system of this invention requires a two-step process: preparation of the aqueous core and housing; and preparation of the final suppository incorporating the aqueous core. Each is an independent, discrete step and the methods employed for the final step are not dependent on the methods employed for the first step.

Figures 2, 3:
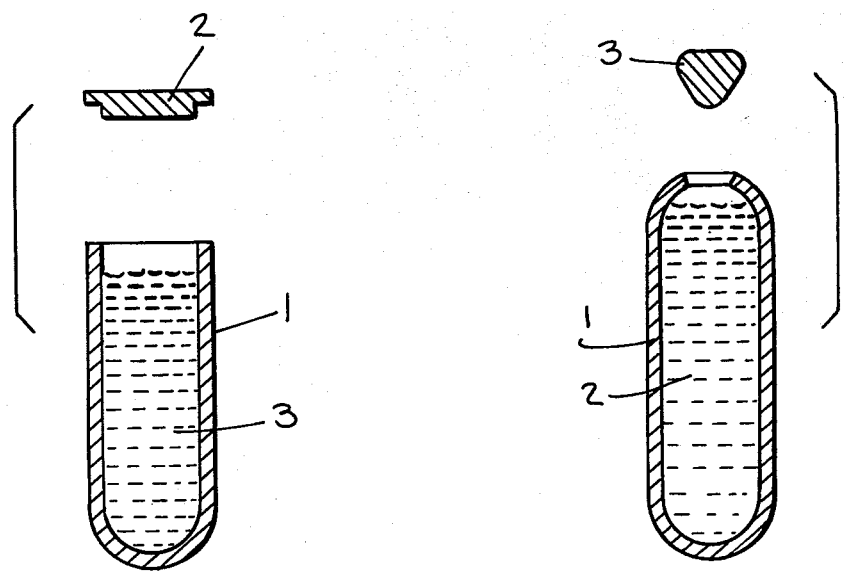
FIG. 2 represents a cross-section of one embodiment of the aqueous core wax housing of the novel device of this invention, comprising a cup-shaped shell, 1, and a closure, 2, which is sealed to 1 after filling with water, 3.
FIG. 3 represents a cross-section of another embodiment of the aqueous core wax housing, 1, of the invention which after filling with water, 2, can be closed with a drop of molten waxy material, 3.

In preparation of the aqueous core and its housing, hollow shells composed of any of a variety of water insoluble, low melting (35°–37° C.) waxy type material are prepared by either dip coating, such as in hard gelatin capsule manufacture or by spin molding as practiced in plastics fabrication. Housings such as shown in FIGS. 2 and 3 are prepared by this process. They are filled with the aqueous media and the ends are sealed by placing the end-cap, 2, (FIG. 2) in place and applying a small amount of heat to the cap to effect a seal (FIG. 2) or by placing a small drop of molten waxy material 3, (FIG. 3) over the aperture to form a seal (FIG. 3).

Alternatively, frozen pellets of the aqueous material, flash frozen by conventional methods, are dip coated while in the frozen state in a molten bath of one of the waxy materials.

As an alternative to the frozen pellets of aqueous material, aqueous cross-linked polymeric gelatinous pellets, shaped as desired, are dip coated as described above. Examples of such pellets are divalent or trivalent metal alginate gels, sodium borate-poly(vinyl alcohol) gels and neutralized carboxyvinyl polymer gels.

In preparing the final suppository form of the drug delivery device of this invention, the aqueous containing cores prepared as described above are coated with a mixture of drug and some water dispersible excipient. In addition, if a controlled release type of preparation is desired, osmotic active agents are included and the whole is finally coated with a semi-permeable membrane.

In one method, hollow shells having an outer shape and dimensions of conventional rectal or vaginal suppositories, and an inner cavity dimension sufficient to accept one of the aqueous cores described above are prepared. The shells are fabricated from mixtures of drug and a water soluble/dispersible ingredient such as polyethylene glycol and typically the drug component represents from 0.1-20% by weight. The open end of the device is sealed at the time of manufacture with a low melting water insoluble waxy material in a manner so as not to cause melting of the aqueous core housing.

Alternatively, the hollow shells described above can be prepared from a mixture of drug and gelatin in the form of a telescoping two part shell to permit facile manufacture.

The aqueous core and housing may also be encapsulated in a soft gelatin shell containing dispersed drug using conventional techniques for forming soft gelatin capsules.

The aqueous core and housing may also be coated with a concentrated aqueous solution containing drug and water soluble polymeric or waxy material by dip coating.

Any of the foregoing devices may also include osmotic agents in the drug matrix in which event the shaped device is finally coated with a semi-permeable membrane such as cellulose acetate, polyvinyl acetate, ethylene vinyl acetate or the like.

What is claimed is:

1. A drug delivery system comprising an aqueous core in a waxy housing, which housing melts at body temperature, surrounded by a matrix, shaped and sized for rectal or vaginal suppository use, comprising drug which is solubilized by the aqueous solution contained in the waxy core and water soluble or dispersible excipients.

2. The drug delivery system of claim 1, wherein the waxy housing of the aqueous core is composed of a water insoluble waxy material, melting at 35°–37° C. selected from the group consisting of theobromo oil, an eutectic mixture of mono-, di and triglycerides, a mixture of higher melting fractions of coconut oil and palm kernel oil, and a mixture of triglycerides of saturated vegetable fatty acids and monoglycerides.

3. The drug delivery system of claim 2 wherein the matrix surrounding the aqueous core comprises drug, water-soluble or water dispersible excipients selected from the group consisting of polyethylene glycol, gelatin, starch, lactose and cellulosic derivatives.

4. The drug delivery system of claim 3 wherein the matrix also comprises an absorption promoter selected from the group consisting of salicylic acid or derivatives, benzalkonium chloride and sodium glycocholate.

5. The drug delivery system of claims 3 or 4, wherein the matrix also comprises osmotic-active agents selected from the group consisting of sodium chloride, mannitol and sucrose and is coated with a semi-permeable film selected from cellulose acetate, polyvinyl acetate and ethylene vinyl acetate.

* * * * *